(12) United States Patent
Butler et al.

(10) Patent No.: US 8,167,429 B1
(45) Date of Patent: May 1, 2012

(54) OPHTHALMIC EXAMINATION SYSTEM WIRELESS INTERFACE DEVICE

(75) Inventors: Kevin A. Butler, Downers Grove, IL (US); Michael C. Whittenburg, Chicago, IL (US)

(73) Assignee: M&S Technologies, Inc., Skokie, IL (US)

( * ) Notice: Subject to any disclaimer, the term of this patent is extended or adjusted under 35 U.S.C. 154(b) by 0 days.

(21) Appl. No.: 12/481,272

(22) Filed: Jun. 9, 2009

Related U.S. Application Data (60) Provisional application No. 61/060,245, filed on Jun. 10, 2008.

(51) Int. Cl.
*A61B 3/00* (2006.01)
*A61B 3/10* (2006.01)

(52) U.S. Cl. .................. 351/246; 351/205; 351/221

(58) Field of Classification Search .................. 351/246, 351/205, 210–211, 200, 221–223, 237, 239, 351/241
See application file for complete search history.

(56) References Cited

U.S. PATENT DOCUMENTS

| | | | |
|---|---|---|---|
| 4,803,312 A | 2/1989 | Britos | |
| 5,249,121 A | 9/1993 | Baum et al. | |
| 5,530,493 A | 6/1996 | Suzuki | |
| 5,914,772 A | 6/1999 | Dyer | |
| 6,731,683 B1 | 5/2004 | Fiedler et al. | |
| 6,976,216 B1 | 12/2005 | Peskin et al. | |
| 7,364,297 B2 | 4/2008 | Goldfain et al. | |
| 2002/0059257 A1 | 5/2002 | Matsumura et al. | |
| 2003/0151721 A1* | 8/2003 | Lai et al. ................. | 351/212 |
| 2005/0036109 A1* | 2/2005 | Blum et al. ............... | 351/168 |
| 2005/0200808 A1* | 9/2005 | Wyatt ....................... | 351/246 |
| 2008/0187033 A1 | 8/2008 | Smith | |
| 2009/0241042 A1 | 9/2009 | Nordstrom | |
| 2010/0265462 A1 | 10/2010 | Nordstrom | |

* cited by examiner

*Primary Examiner* — Dawayne Pinkney
(74) *Attorney, Agent, or Firm* — Fay Sharpe LLP

(57) ABSTRACT

An automated ophthalmic system is disclosed that is utilized to examine the eyes of a subject. A refraction system measures the refractive error of each eye and identifies a lens to correct the refractive error detected. A display presents one or more optotypes to the subject to ascertain the refractive error. An interface device receives a wireless signal from the refraction system, converts the wireless signal into one or more ASCII characters, and communicates the one or more ASCII characters to the display to present the one or more optotypes.

18 Claims, 5 Drawing Sheets

OPHTHALMIC EXAMINATION SYSTEM WIRELESS INTERFACE DEVICE

This application claims the priority benefit of U.S. application Ser. No. 61/060,245, filed Jun. 10, 2008, the disclosure of which is incorporated herein by reference.

BACKGROUND

The present exemplary embodiments relate generally to ophthalmic examination systems. In one particular application, a wireless interface device is utilized to facilitate communication between a phoroptor and a display within the ophthalmic examination system. However, it is to be appreciated that the present exemplary embodiment is also amenable to other like applications.

An eye examination is a battery of tests performed by an optometrist or ophthalmologist to assess a subject's vision and ability to focus on and discern objects. An automated ophthalmic exam system can be employed to aid in the determination of a subject's refractive error and to identify an appropriate lens prescription to correct such error. In one example, an automated ophthalmic system includes a phoroptor and an eye chart. The phoroptor is used to present powered lenses in front of a subject's eyes. The eye chart can be read by the subject via the phoroptor to aid the determination of visual acuity during the test.

The phoroptor can be employed to refine the prescription, identified via the refraction system, to one which provides the subject with the best vision. The lenses within a phoroptor refract light in order to focus images on the subject's retina. By changing these lenses, the examiner is able to determine the spherical power, cylindrical power, and/or cylindrical axis necessary to correct a subject's refractive error. From the measurements taken, a corrective lens prescription can be identified that contains at least six numerical specifications (three for each eye): sphere, cylinder and axis.

An eye chart is used to measure visual acuity when viewed by the subject via the phoroptor. Types of eye charts can include a Snellen chart, a tumbling E chart, and a Landolt C chart. Charts usually display several rows, wherein each row contains different sized test symbols or optotypes. The subject is asked to identify the optotypes on the chart, usually starting with large rows and continuing to smaller rows until the optotypes cannot be reliably identified any longer. Charts can be employed with very young children or illiterate adults that are incapable of letter recognition. One version uses simple pictures or patterns (e.g., an apple, a house, a square, and a circle) that are selected based upon the results of recognition trials. The tumbling E chart has the block letter "E" turned in different orientations, wherein the subject simply indicates which direction each "E" is facing. Similarly, the Landolt C chart has rows of circles with different segments missing and the subject describes where each broken piece is located.

Eye charts can be presented via a computer-based display and/or a chart projector in concert with the automated ophthalmic exam system. There are several potential advantages such as more precise measurement and less examiner induced bias in the examination. Compatibility issues can arise, however, when communication is attempted between a refraction system and a computer-based eye chart produced by disparate manufacturers. In particular, automated ophthalmic exam systems generally employ proprietary protocols to communicate between such components. Accordingly, systems and methods are needed to facilitate communication between automated ophthalmic exam system components, regardless of the manufacturer.

BRIEF SUMMARY OF THE INVENTION

In one aspect, an automated ophthalmic system is utilized to examine the eyes of a subject. A refraction system measures the refractive error of each eye and identifies a lens to correct the refractive error detected. A display presents one or more optotypes to the subject to ascertain the refractive error. An interface device receives a wireless signal from the refraction system, converts the wireless signal into one or more ASCII characters, and communicates the one or more ASCII characters to the display to present the one or more optotypes.

In another aspect, a method is employed to facilitate communication between a refraction system and a display within an automated ophthalmic system. An interface is connected device between the refraction system and the display. A wireless communication is sent from the refraction system to the interface device. If the wireless signal does not have a header from a remote control, the wireless signal is decoded as sent from a refraction system if the wireless signal is not from a remote control. The decoded wireless signal is converted to an ASCII character and sent to the display.

In yet another aspect, an interface device is utilized to communicate data between a refraction system and a display within an automated ophthalmic system. A wireless detector receives a wireless signal from the refraction system. A data port facilitates communication between the display and the interface device, wherein an ASCII converter associates one or more ASCII characters with the wireless signal. An I/O controller communicates the one or more ASCII characters from the interface device to the display.

DETAILED DESCRIPTION

Figure 1:
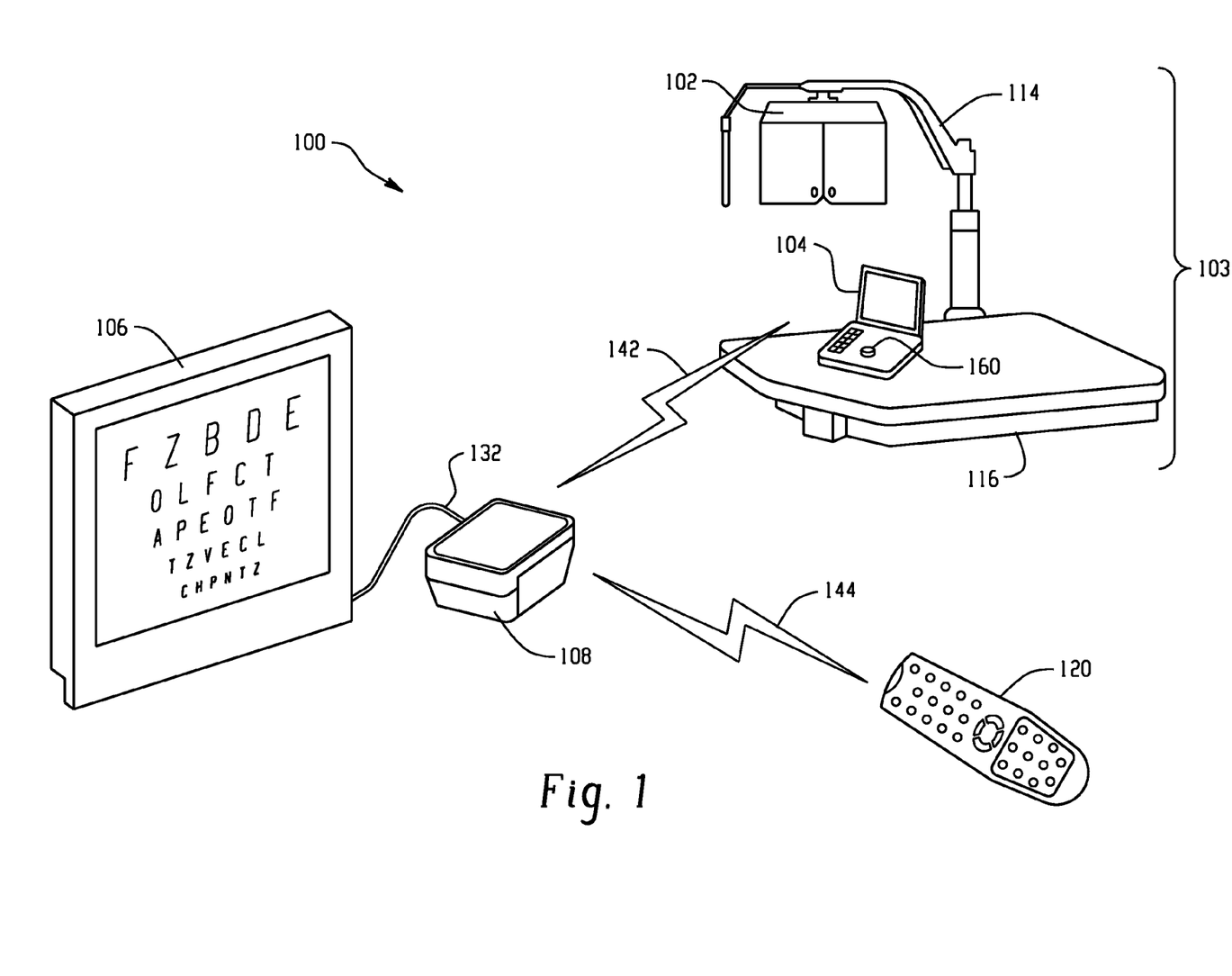
FIG. 1 illustrates an automated ophthalmic exam system, in accordance with an exemplary embodiment.

FIG. 1 illustrates an automated ophthalmic examination system 100 that is utilized to perform eye examinations on subjects. A phoroptor 102 is operated via a user interface 104 to measure a subject's refractive error and to determine an appropriate corrective lens for compensation thereof. The phoroptor 102 and the user interface 104 comprise a refraction system 103 that evaluates vision by presentation of images via a display 106, as viewed by the subject through a plurality of disparate lenses. The user interface 104 is coupled to the display component 106 via an interface device 108, which is connected to the display 106 via a hardwire cable 132. The refraction system 103 and a remote control 120 can communicate with the interface device 108 via a wireless signal 140 and 142 respectively.

Substantially any design, such as coaxial, twisted pair, etc., is contemplated for the cable 132. Further, substantially any pin configuration and/or connector such as an RJ45 connector, a 7-pin DIN connector, a USB connector, a DB9 connector, a DB25 connector, etc. can be employed to couple the interface device 108 and the display 106 via the cable 132. Substantially any protocol or standard can be utilized to communicate via the cable 132 such as RS-232, RS-485, Ethernet, etc. to facilitate communication therebetween. Any wireless protocol such as IEEE 802.11b, wireless Ethernet, or Wi-Fi communicated at any frequency such as RF, infrared, visible light, and/or acoustic energy is contemplated for the wireless signals 142 and 144.

The phoroptor 102 can provide automated functionality to facilitate intuitive operator usage. In one aspect, a dial 160 can allow an operator to quickly change sphere, cylinder and axis powers with one hand to provide a reliable examination. The user interface 104 can present data to a user via a touch screen (e.g., a TFT LCD) and can include one or more slots for data transfer via a card, stick jump drive or equivalent memory device. The user interface 104 can provide operation and question guidance to an operator within an examination proceeding. In this manner, inexperienced operators can provide accurate and reliable ophthalmic examinations by following instructions provided on the user interface 104. The user interface 104 can present near vision charts and/or program/operation messages to facilitate selection of one or more examination protocols and/or specific eye charts for presentation via the display 106. An arm 114 can support the phoroptor 102 to allow articulation along a rotational and/or a vertical axis to accommodate a plurality of subject sizes.

In one approach, a controller 116 can receive communication from the refraction system 103, generate a wireless signal related thereto and transmit the wireless signal to the interface device 108. Alternatively or in addition, the controller 116 can contain one or more ports to connect disparate peripheral devices to the refraction system 103. Such peripheral devices can include a mouse, a pointer, a roller ball, a printer, and/or a plotter, for example. In one embodiment, the peripheral device is an autorefractor and/or a lensometer. Such devices can provide an objective measurement of a subject's refractive error and prescription for corrective lenses by examining the subject's eyes and/or corrective lenses respectively.

The display 106 can include a processor to provide processing support for the execution of the transfer and processing of the input signals and/or ASCII characters. It is to be appreciated that although a standalone architecture is illustrated, that any suitable computing environment can be employed in accordance with the present embodiments. For example, computing architectures including, but not limited to, stand alone, multiprocessor, distributed, client/server, minicomputer, mainframe, supercomputer, digital and analog can be employed in accordance with the present embodiment.

The processor can include a processing unit (not shown), a system memory (not shown), and a system bus (not shown) that couples various system components including the system memory to the processing unit. The processing unit can be any of various commercially available processors. Dual microprocessors and other multi-processor architectures also can be used as the processing unit. The system bus can be any of several types of bus structure including a memory bus or memory controller, a peripheral bus, and a local bus using any of a variety of commercially available bus architectures. The memory includes read only memory (ROM) and random access memory (RAM). A basic input/output system (BIOS), containing the basic routines that help to transfer information between elements within the computer, such as during start-up, is stored in ROM.

The processor can further include a hard disk drive, a magnetic disk drive, e.g., to read from or write to a removable disk, and an optical disk drive, e.g., for reading a CD-ROM disk or to read from or write to other optical media. The processor typically includes at least some form of computer readable media. Computer readable media can be any available media that can be accessed by the processor. By way of example, and not limitation, computer readable media may comprise storage media and communication media. Storage media includes volatile and nonvolatile, removable and non-removable media implemented in any method or technology for storage of information such as computer readable instructions, data structures, program modules or other data. Storage media includes, but is not limited to, RAM, ROM, EEPROM, flash memory or other memory technology, CD-ROM, digital versatile disks (DVD) or other magnetic storage devices, or any other medium which can be used to store the desired information and which can be accessed by the processor.

Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above can also be included within the scope of computer readable media.

A number of program modules may be stored in the drives and RAM, including an operating system, one or more application programs, other program modules, and program non-interrupt data. The operating system in the processor can be any of a number of commercially available operating systems.

A user may enter commands and information into the processor through a keyboard (not shown) and a pointing device (not shown), such as a mouse. Other input devices (not shown) may include a microphone, an IR remote control, a joystick, a game pad, a satellite dish, a scanner, or the like. These and other input devices are often connected to the processing unit through a serial port interface (not shown) that is coupled to the system bus, but may be connected by other interfaces, such as a parallel port, a game port, a universal serial bus ("USB"), an IR interface, etc.

Further, the display 106 can include a monitor or similar unit to present images. The monitor (or other type of display device) is also connected to the system bus via an interface, such as a video adapter (not shown). In addition to the monitor, a processor typically includes other peripheral output devices (not shown), such as speakers, printers etc. The monitor can be employed with the processor to present data that is electronically received from one or more disparate sources. For example, the monitor can be an LCD, plasma, CRT, etc. type that presents data electronically. Alternatively or in addition, the monitor can display received data in a hard copy format such as a printer, facsimile, plotter etc. The monitor can present data in any color and can receive data from the processor via any wireless or hard wire protocol and/or standard.

The processor can operate in a networked environment using logical and/or physical connections to one or more remote computers, such as a remote computer(s). The remote computer(s) can be a workstation, a server computer, a router, a personal computer, microprocessor based entertainment appliance, a peer device or other common network node, and typically includes many or all of the elements described relative to the processor. The logical connections depicted include a local area network (LAN) and a wide area network (WAN). Such networking environments are commonplace in offices, enterprise-wide computer networks, intranets and the Internet.

When used in a LAN networking environment, the processor is connected to the local network through a network interface or adapter. When used in a WAN networking environment, the processor typically includes a modem, or is connected to a communications server on the LAN, or has other means for establishing communications over the WAN, such as the Internet. In a networked environment, program modules depicted relative to the processor, or portions thereof, may be stored in the remote memory storage device. It will be appreciated that network connections described herein are exemplary and other means of establishing a communications link between the processors may be used.

The display 106 can present images to be viewed by the subject for acuity testing. In one example, letters, numbers, lines, pictograms, dots, tumbling Es, Landolt Cs, and/or ETDRS charts can be selected. Such optotypes can be presented in a plurality of sizes according to disparate testing configuration protocols. Alternatively or in addition, contrast sensitivity can be measured by presenting optotypes in a plurality of darkness levels. The display can be a backlit flat screen device such as an LCD or plasma monitor. Additional tests such as red-green and red-blue anaglyph stereo testing can also be presented via the display 106 for use with appropriate glasses. In one embodiment, the display 106 can be mounted to a wall or other vertical surface to provide height appropriate chart presentations.

The remote control 120 can be utilized to replace or supplement the functionality of the refraction system 103 (e.g., to select one or more tests, optotype sizes, fixation, etc.). Commands can be selected by one or more pushbuttons to initiate functions of the display 106. The remote control 120 can utilize a frequency around 40 KHz to emit the wireless signal 144. In one approach, the remote control 120 modulates the signal 144 with signals of different frequency. The interface device 108 can receive the wireless signal 144 via an IR detector for demodulation by applying appropriate frequency filters to separate the respective signals.

The interface device 108 is utilized to emulate a chart projector or proprietary computer display that is typically used with the refraction system 103. In this manner, the refraction system 103 can operate a non-projector device, such as the display 106, via equivalent commands to present desired images to an exam subject. Thus, the interface device 108 eliminates the need to modify/replace the communication protocol of the refraction system 103 and allows communication with any models associated with the display 106 for presentation of images thereof. In one example, the interface device 108 includes a processing component that identifies communication changes from both the refraction system 103 and the remote 120.

The interface device 108 receives wireless signals via an IR detector. Once received, the interface device 108 determines if they are sent from the refraction system 103, the remote control 120 or another source. In one example, the interface device 108 first attempts to decode the incoming wireless signal as if it was sent from the remote control 120. If the signal, however, does not have the appropriate header, the interface device 108 can attempt to decode the signal as though it was sent from the refraction system 103. If it is determined that the signal is not from either source, it is ignored.

Thus, the display 106 does not directly read communication sent from the refraction system 103. Instead, ASCII characters are received from the interface device 108 to provide greater isolation and error handling throughout the automated ophthalmic exam system 100. The interface device 108 can also be utilized to convert a first protocol from the refraction system 103 to a second protocol for communication to the display 106. In one example, the interface device 108 is coupled to the refraction system 103 via a wireless detector and the display 106 via a serial connection. The wireless signal 142 is converted by the interface device 108 to an ASCII character, which is sent to the display via the communication cable 132. In one embodiment, information within the wireless signal 142 is associated with the ASCII character via a lookup table.

In one embodiment, the interface device 108 includes two connections: (1) a standard USB type-B connector to couple the interface device 108 to the display 106 via the communication cable 132 (e.g., standard USB type-B to USB type-A) and (2) a 38 KHz IR detector that outputs a 5 volt logic signal to a microcontroller. The IR detector can be placed behind an infrared transparent panel at one end of an enclosure. The interface device 108 can utilize a flash microcontroller, such as a Microchip Technology Model 18F1320 with 8K of flash memory stored on an interface program. Power (5VDC) can be delivered to the interface component 108 via the USB connector, to eliminate the need for an external power adapter.

The interface device 108 can communicate with the display 106 via a hardware USB port, which emulates a serial port. In this manner, the hardware USB port that connects the display 106 to the interface device 108 utilizes serial communication protocols and has a serial port software assignment (e.g., COM1, COM2, COM3, etc.). For this purpose, the interface device 108 can include a USB interface chip (FT232RL) from Future Technology Devices International, for example. The FT232RL can emulate a standard RS-232 serial port to the PC, wherein suitable drivers are automatically installed if the display is connected to the Internet. In one example, the interface device 108 communicates with the display 106 via an RS-232 protocol at 9600 baud, no parity, 1 stop bit, wherein no flow control is utilized. It is to be appreciated that a plurality of disparate connectors and support for multiple communication standards, wired or wireless, are contemplated to facilitate connection of substantially any model refraction system with substantially any model display.

Figure 2:
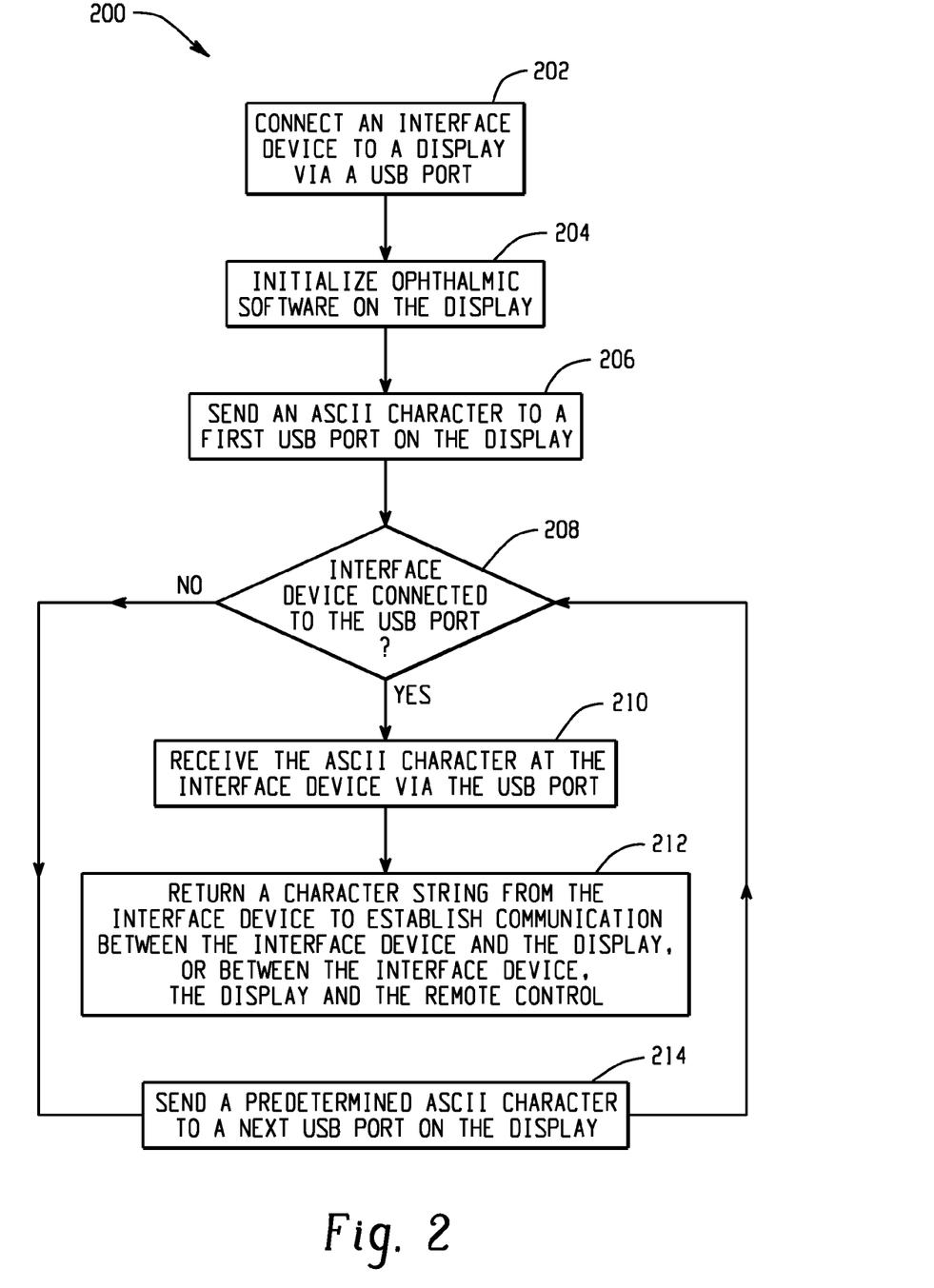
FIG. 2 illustrates a method to establish communication between a wireless interface device and a display within the automated ophthalmic exam system, in accordance with an exemplary embodiment.

FIG. 2 illustrates a method to establish communication between an interface device (e.g., 108) and a display (e.g., 106). At reference numeral 202, an interface device is connected to a display via a hardware USB port. The USB port can be coupled to an interface chip (or equivalent) within the display to emulate a serial port as viewed by ophthalmic software running on the display. At 204, the ophthalmic software is initialized on the display and, at 206, a predetermined ASCII character is sent, via software, to a first serial port residing on the display. At 208, a determination is made whether an interface device is connected to the serial port through which the ASCII character was sent. If so, at 210, the ASCII character is received at the interface device via the USB port.

At 212, a character string is returned from the interface device to (1) establish communication between the interface device and the display and (2) indicate the components in which the interface device is in wireless communication. In one example, the character string contains a first group of characters if the interface device is receiving communication from the refraction system and a second group of characters if the refraction system is receiving messages from a remote control. If the character string contains both the first and second group of characters, it is an indication that both the refraction system and the remote control are in communication with the interface device.

Thus, when the display receives the character string message, it verifies that a particular serial port is connected to the interface device and the communication to third party devices via the interface device. If the interface device is not connected to the serial port through which the ASCII character was originally sent, at 214, a predetermined ASCII character is sent to a next serial port on the display. If an ASCII character is sent to every serial port on the display and does not receive a return character string, an error is displayed. In this manner, the interface device can be automatically discovered, regardless of the serial port it is connected to on the display.

Figure 3:
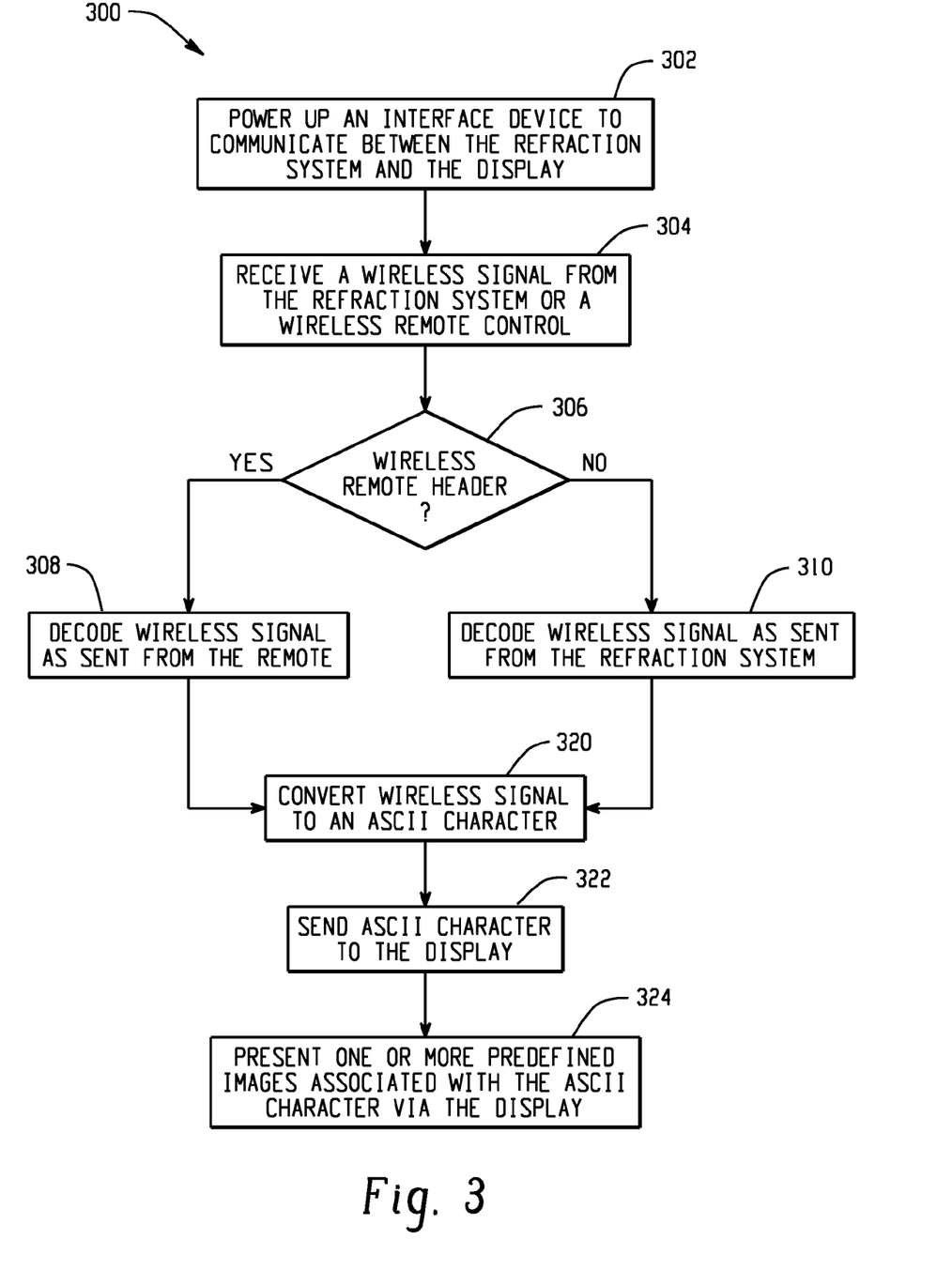
FIG. 3 illustrates a method to present an image from a refraction system to the display via a wireless interface device, in accordance with an exemplary embodiment.

FIG. 3 illustrates a method to present one or more predefined images via a display. At 302, an interface device is powered up to communicate between a refraction system and a display. At 304, a wireless signal is received from the refraction system or a wireless remote control. If a wireless remote header is received at 306, it is decoded as a wireless signal from the remote control at 308. At 320, the decoded wireless signal is converted to an ASCII character, which is sent to the display at 322. At 324, one or more predefined images associated with the ASCII character are presented via the display.

If, however, the wireless signal is not from the wireless remote control, it is decoded as sent from the refraction system at 310. The conversion of the wireless signal to one or more ASCII characters can come from a predefined configuration, such as a look up table and/or memory store. At 322, the one or more ASCII characters are sent to the display and presented and associated with one or more predefined images to be presented via the display at 324. In this manner, the wireless signal received by an interface device can be correlated to one or more ASCII characters for consumption via the display. Such message can be transmitted in a predefined format (e.g. 9600 baud, 8 bits, no parity with one stop bit) and can consist of a hexadecimal representation of the information sent by the display.

The display receives this message and changes the displayed chart as needed. The display, however, does not need to acknowledge the messages that are sent by the interface device. In one embodiment, the only time the display transmits to the interface device is during initialization when it sends an ASCII character command to locate the interface device. Once this configuration is complete and the use of the interface device is selected, the user will have no further steps. The interface device and display are prepared to communicate and work together anytime the systems are turned on. Thus, when an operator presses a button on the refraction system, the appropriate chart will be shown in the display via the interface device. In addition, an operator can have the ability to simultaneously operate the display via a remote control to access various charts and/or functionality that may not be available via the refraction system.

Figure 4:
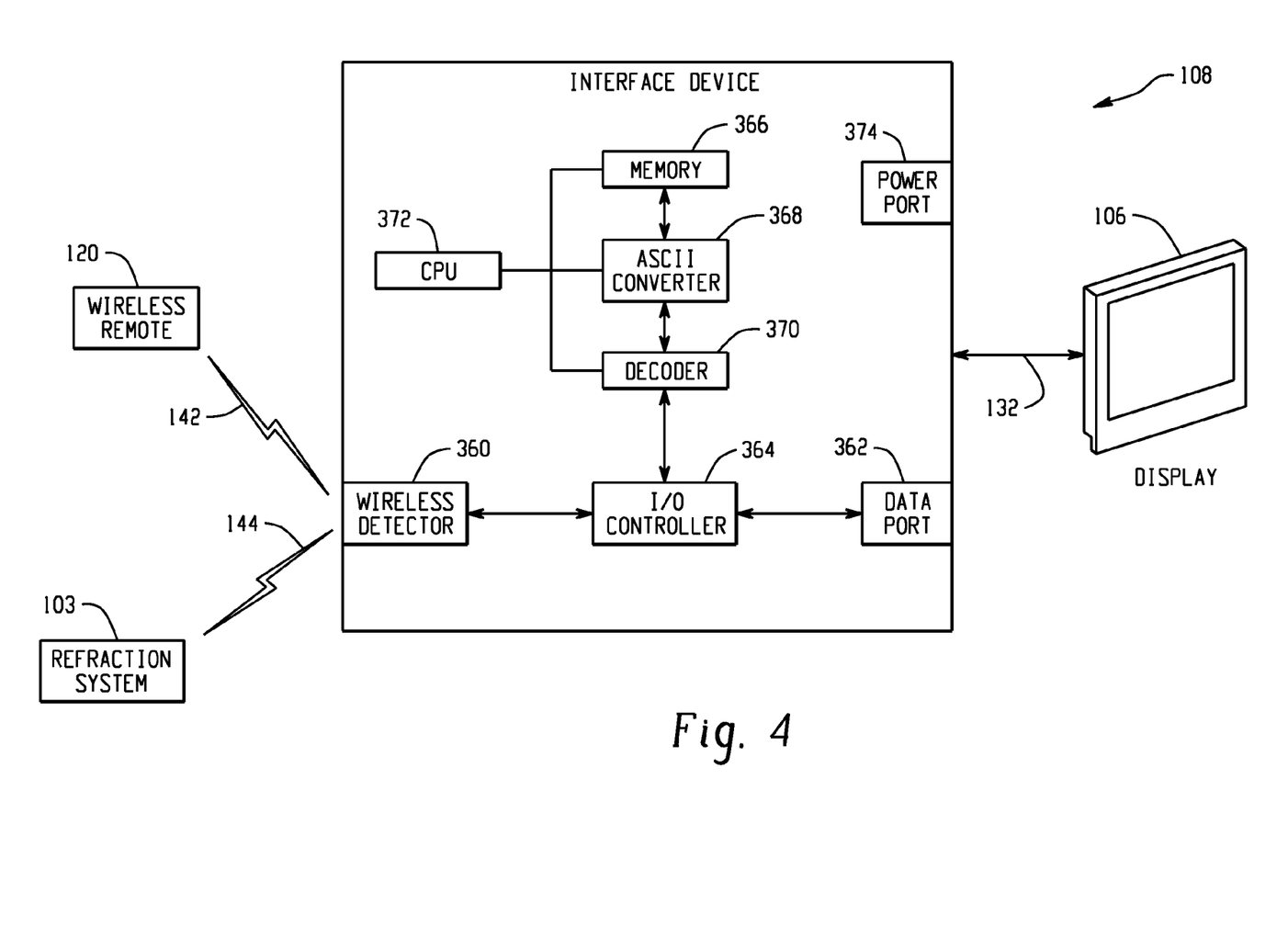
FIG. 4 illustrates an exemplary embodiment of the wireless interface device.

FIG. 4 illustrates the components within the interface device 108. Wireless signals are received from the refraction system 103 by the interface device 108 via a wireless detector 360. In one embodiment, the wireless detector 360 detects infrared signals at around 40 KHz. Signals received by the wireless detector 360 can be communicated to a data port 362 and on to the display 106 via an I/O controller 364. The data port 362, in one embodiment, is a USB port that facilitates communication of ASCII strings via a particular protocol. Signals received via the wireless detector 360 are communicated to a decoder 370 to read the information communicated via the carrier wave of the wireless signal. Standard algorithms can be employed to ascertain the wireless signal protocol and the information contained therein (e.g., within each packet, etc.).

Power can be delivered to the interface device 108 from an external source via the cable 132 through the data port 362. In one example, a USB cable is employed. In alternative embodiments, a serial or other cable is used that does not deliver power to the interface device 108. In such cases, an optional power port 374 delivers power from an external source to the interface device 108.

The I/O controller 364 is utilized to govern the flow of data between the wireless detector 360 and the data port 362 and on to the refraction system 103 and the display 106. If a predefined input is detected, an ASCII converter 368 is utilized to convert the input (e.g., from the wireless signal) into one or more ASCII characters for communication via the data port 362. A memory store 366 can be utilized by the ASCII converter 368 to obtain a table of associated input values with ASCII characters. In one example, the memory store 366 contains one or more look up tables that contain information to allow the storage, editing and retrieval of such information.

A CPU 372 is utilized to provide processing support for the execution of the transfer and processing of the wireless signals and/or ASCII characters within the interface device 108. A processor (e.g., the CPU 372) can be employed to support the systems and methods herein including the refraction system 103, the display 106, the interface device 208 and the methods 200 and 300. The CPU 372 can include the same or similar functionality as described with regard to the processor within the display 106, described above.

In one example, the CPU 372 executes exemplary pseudo code to facilitate functionality of the interface device 108, as outlined below.

1. The code begins by initializing the hardware, then calling a main( ) function.
2. The main( ) function initializes various timers and blinks a red LED on the interface device 108 ten times quickly.
3. The main( ) function contains a infinite "while" loop, which watches for the signal from the infrared detector to go active or for a command to be received from the display 106 via the USB port.
4. If a command is received, the system calls a parse_cmd( ) function. This function looks for a first predetermined ASCII character and responds by sending back a predetermined string. The system also looks for a second predetermined ASCII character and prints the software version. Any other command is ignored.
5. Once the detector goes active, the code starts checking the signal at 10 μsec intervals.
6. If the signal stays active for at least 470 μsec, then the signal is assumed to be coming from the remote control 120. If the signal is active for 470 μsec or less, it is assumed to be coming from the refraction system 103.
7. If it is assumed to be a signal from the refraction system 103, then a function try_refraction system( ) is called.
8. Otherwise, the system continues to receive the signal 144 from the remote control 120 by sampling the signal from the wireless detector 360 at 880 μsec intervals for the length of the message.
9. The samples are then used to compute a unique 8-bit value for the signal.

10. The samples are also checked to verify that the signal is valid and meets all predefined requirements. If it doesn't, then the signal is interpreted as noise or from another source. Accordingly, such data is discarded.

11. If the samples are valid, however, then the unique value is converted via a lookup table to match the values expected by the display 106.

12. The final value is then output via the data 362 port in hexadecimal format, preceded by an identifier value of 0xc4. This initial value is used to communicate to the display 106 that the next code is coming from the remote control 120 instead of the refraction system 103. The system then goes back to the beginning of the infinite "while" loop and to look for the next IR message.

13. If the try_refraction system( ) function was called, the system receives one or more bytes of data by timing the IR pulses. If the pulse is greater than a predetermined length of time, then the bit is a "one." Otherwise, it is a "zero."

14. Once the one or more bytes are received from the refraction system 103, an error check is performed on them and, if there is no problem, they are output via the data port 362 in hexadecimal format to the display 106. No preceding value is added to the refraction system 103 output because the refraction system 103 sends its own identifier in every message.

15. The system then goes back to the beginning of the infinite "while" loop and starts looking for the next IR message (e.g., from the refraction system 103 or the remote control 120).

Figure 5:
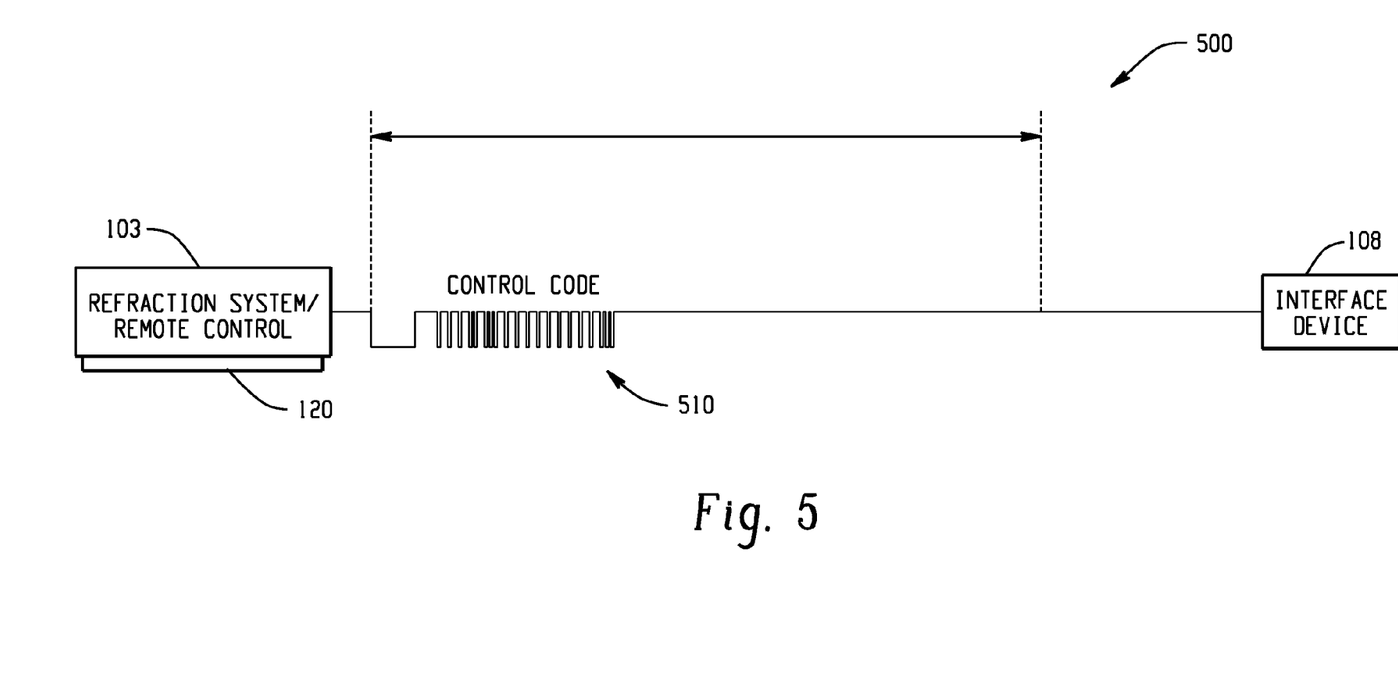
FIG. 5 illustrates a communication sequence between the refraction system and the display, in accordance with an exemplary embodiment.

FIG. 5 illustrates a communication sequence 500 between the refraction system 103 and/or the remote control 120 with the interface device 108. As discussed above, the communication is then sent from the interface device 108 to the display 106. To initiate the communication sequence 500, the refraction system 103 or remote control 120 can output a wireless control code 510 to change or modify one or more images that are presented to a subject via the display 106. The control code 510 can be transmitted via a wireless carrier wave and received by the interface device 108 via the wireless detector 360.

In one example, the control code 510 includes a header, a refraction system code, a chart code, and a channel code. The header can be utilized to indicate the beginning of the transmission of the control code. Once the header is sent, the refraction system code can be a preset bit length to indicate the model of refraction system utilized for communication. The chart code can be sent after the header and the refraction system code to indicate the type of images to present on the display 106. Further, the chart code can be associated with display functionality such as screen brightness, color, image contrast, backlight, and/or program selection. The channel code corresponds to one of a plurality of channels that can be utilized for wireless communication. In one example, eight channels can be selected to correspond to associated wireless channels of the refraction system 103.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. An automated ophthalmic system that is utilized to examine the eyes of a subject, comprising:
    a refraction system that measures the refractive error of each eye and identifies a lens to correct the refractive error detected, and emits a wireless signal;
    a display that presents one or more optotypes to the subject to ascertain the refractive error;
    a remote control that emits a wireless signal that is received by the interface device to replace or supplement the signal sent from the refraction system, the wireless signal is communicated to the display via the interface device; and
    an interface device that is configured to receive the wireless signal from at least one of the refraction system or remote control, converts the wireless signal into one or more ASCII characters, and communicates the one or more ASCII characters to the display to present the one or more optotypes.

2. The system of claim 1, wherein the wireless signal is transmitted via an infrared carrier wave.

3. The system of claim 1, wherein the optotype presented is one or more of a letter, a number, a tumbling E, a Landolt C, a pictogram, and ETDRS chart, a dot, and a grid.

4. The system of claim 1, wherein the interface device further includes a wireless detector that receives a wireless signal from at least one of the refraction system and the remote control.

5. The system of claim 1, wherein the interface device further includes an ASCII converter that converts the wireless signal received by the wireless detector into one or more ASCII codes that are output to the display.

6. The system of claim 5, wherein the interface device further includes a lookup table that associates information within the wireless signal to at least one ASCII symbol for consumption via the display.

7. A method to facilitate communication between a refraction system and a display within an automated ophthalmic system, comprising:
    connecting an interface device between the refraction system and the display;
    sending a wireless communication from the refraction system to the interface device;
    determining if the wireless signal does not have a header from a remote control;
    decoding the wireless signal as sent from a refraction system if the wireless signal is not from a remote control;
    converting the decoded wireless signal to an ASCII character; and,
    sending the ASCII character to the display.

8. The method of claim 7, further including:
    decoding the wireless signal as sent from the remote control if a remote control header is identified.

9. The method of claim 7, further including:
    initializing ophthalmic software on the display; and
    sending an ASCII character to a first serial port on the display.

10. The method of claim 7, further including:
    presenting one or more predefined optotypes associated with the ASCII character via the display.

11. The method of claim 9, further including:
    receiving the ASCII character at the interface device via the serial port; and,
    returning a character string from the interface device to establish communication between the interface device and the display.

12. An interface device that is utilized to communicate data between a refraction system and a display within an automated ophthalmic system, comprising
- a wireless detector that receives a wireless signal from either the refraction system or a remote control;
- a data port that facilitates communication between the display and the interface device;
- an ASCII converter that associates one or more ASCII characters with the wireless signal and decodes the wireless signal based at least in part upon the source of the wireless signal; and
- an I/O controller that communicates the one or more ASCII characters from the interface device to the display.

13. The device of claim 12, wherein the interface device further includes a memory that contains a lookup table to associate one or more predefined wireless signals with one or more ASCII characters.

14. The device of claim 12, wherein the ASCII character is associated with a particular chart, the chart contains a plurality of optotypes.

15. The device of claim 12, wherein the ASCII character is related to the functionality of the display.

16. The device of claim 12, wherein the ASCII character is associated with at least one of a back light of the display, a contrast of the display, and a filter of the display.

17. The device of claim 12, wherein the ASCII converter
- reads the header of the wireless signal; and
- decodes the wireless signal as sent from the remote control if a remote control header is identified.

18. The device of claim 12, wherein the wireless signal is transmitted via a carrier wave that has a frequency of about 40 KHz.

\* \* \* \* \*